US00PP21663P3

(12) United States Plant Patent
Coiner

(10) Patent No.: US PP21,663 P3
(45) Date of Patent: Jan. 25, 2011

(54) HYBRID TEA ROSE PLANT NAMED 'PINK PROMISE'

(50) Latin Name: *Rosa hybrida*
Varietal Denomination: Pink Promise

(76) Inventor: James W. Coiner, P.O. Box 7217, La Verne, CA (US) 91750

( * ) Notice: Subject to any disclaimer, the term of this patent is extended or adjusted under 35 U.S.C. 154(b) by 312 days.

(21) Appl. No.: 12/287,943

(22) Filed: Oct. 14, 2008

(65) Prior Publication Data

US 2010/0095411 P1 Apr. 15, 2010

(51) Int. Cl.
*A01H 5/00* (2006.01)

(52) U.S. Cl. ..... Plt./137

(58) Field of Classification Search ..... Plt./137

See application file for complete search history.

*Primary Examiner*—Wendy C. Haas
(74) *Attorney, Agent, or Firm*—Christie, Parker & Hale, LLP

(57) ABSTRACT

A new variety of Hybrid Tea suitable for garden decoration, having flowers of pink coloration.

1 Drawing Sheet

Figure 1:
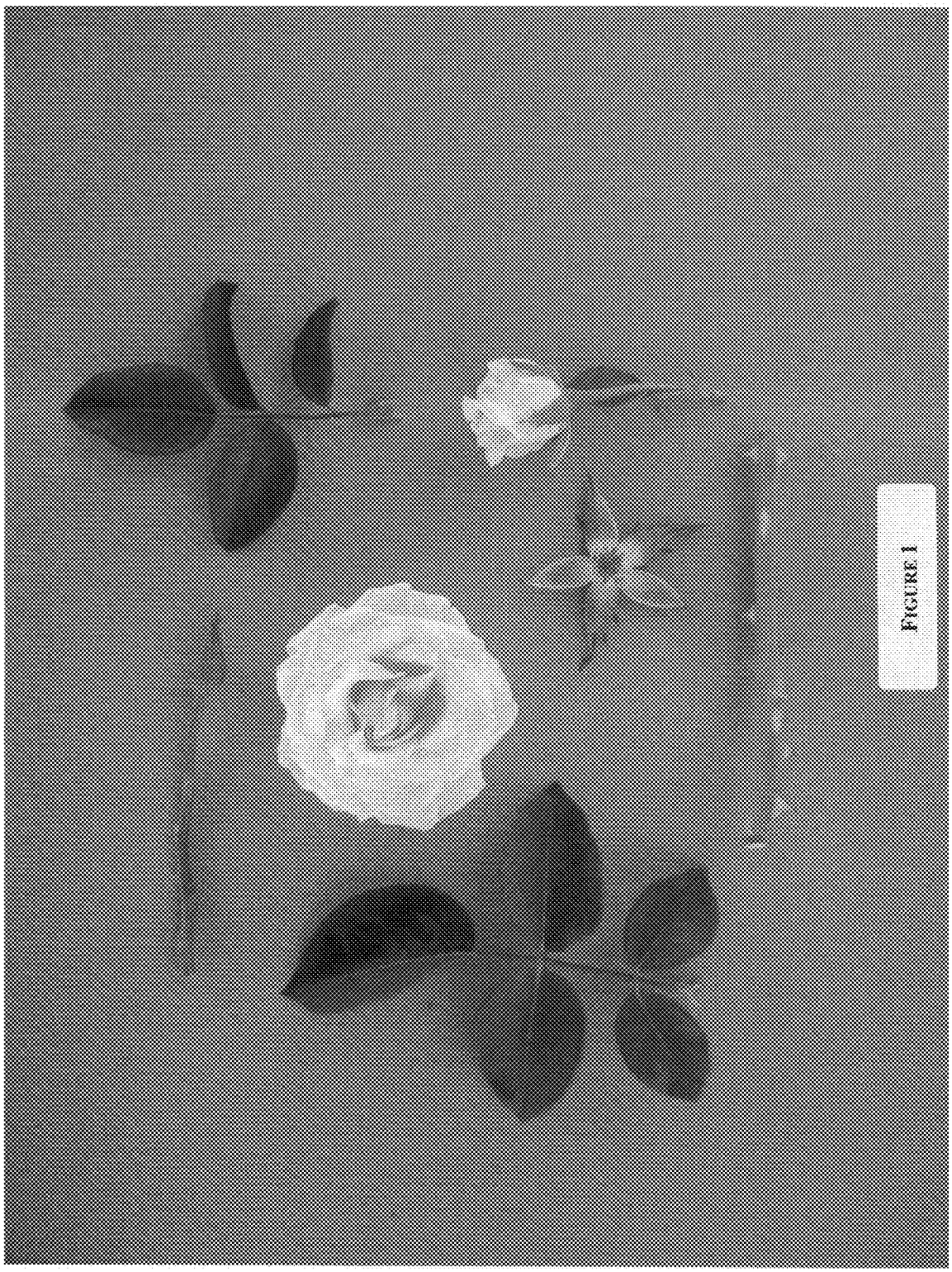

Classification: The present invention relates to a new *Rosa hybrida* plant.

Variety denomination: The new plant has the varietal denomination 'PINK PROMISE'.

BACKGROUND OF THE INVENTION

This invention relates to a new and distinct variety of Hybrid Tea Rose. It has as its seed parent the variety known as an unknown seedling and as its pollen parent the variety known as an unknown seedling.

SUMMARY OF THE INVENTION

Among the features which distinguish the new variety from other presently available and commercial rose cultivars known to the inventor are the combination of characteristics: The plant is an upright growing cultivar, vigorous in nature and form, suitable for outdoor garden decoration.

Asexual reproduction of the new variety by budding as performed in Kern County Calif., shows that the foregoing and other distinguishing characteristics come true to form and are established and transmitted through succeeding asexual propagations. 'Pink Promise' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar 'Queen Elizabeth' (unpatented) by the following combination of characteristics: 'Pink Promise' is a lighter shade of pink in the budded stage, the foliage is a lighter shade of green than 'Queen Elizabeth'.

BRIEF DESCRIPTION OF ILLUSTRATION

The accompanying photograph (FIG. 1) illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors La Verne, Calif. in the month of May. Phenotypic expression may vary with environmental, cultural and climatic conditions, as well as differences in conditions of light and soil.

FLOWER

The new variety sometimes usually bears its flowers singly, usually in clusters of two to three or more several per stem. Flowers may be borne clusters on strong long stems (about 7 to about 9 cm.). Outdoors, the plant blooms abundantly and nearly continuously during the growing season. The flowers have strong spicy fragrance.

BUD

The peduncle is about 1 to about 2 cm. in length, average caliper (about ¼ to about ½ cm. in diameter), and usually erect. It is almost usually smooth, with some stipitate glands, and few hairs and prickles. Peduncle color is near between 138a and 138b sometimes suffused, especially on the side exposed to the sun, with near between 138b and 138c.

Before the calyx breaks, the bud is about 3½ to about 4½ cm. in diameter at the widest point, about 4 to about 5 cm. in length, and pointed in shape with a conspicuous neck. The surface of the bud bears some appendages and glandular bloom, usually with slender bristle-like foliaceous parts extending beyond the tip of the bud about ½ or more of its length. Bud color is near between 56a and 56b sometimes suffused, especially on the side exposed to the sun, with near between 56b and 56c.

The sepals are about 3¼ to about 3½ cm. in length and about ¾ to about 1 cm. in width at the widest point. The outer surface color of the sepal is near between 144a and 143a sometimes often heavily lightly suffused, especially on the side exposed to the sun, with near between 143a and 143b. The inner surface color of the sepal is near between 144a and 143a and covered edged with fine wooly tomentum; sepal margins are lined with some many stipitate glands and hairs.

BLOOM

When fully open, the bloom ranges from about 13 to about 15 cm. in diameter. Petalage is double with about 25 to 30 petals and no petaloids. When partially open, the bloom form is high centered, and the petals are spiraled with petal edges moderately somewhat rolled outward. When fully open, the bloom form is very full, and the petals are tightly cupped with petal edges outward.

PETALS

The substance of the petals is moderately crisp and of moderately thin to medium thickness, with upper surfaces slightly satiny to velvety and under surfaces slightly satiny to velvety to matte. The petals are about 1.2 to about 3.2 cm. in length and about 0.9 to about 4 cm. in width at the widest point.

The outer petals are moderately in shape with apices moderately rounded.

The inner petals are moderately obovate in shape with apices moderately rounded.

OPENED FLOWER

The under and upper surface color of the outer petals is near between 62C and 62D. The upper surface color of the outer petals is near between 62B and 62C.

The under and upper surface color of the intermediate petals is near between 65B and 65C. The upper surface color of the intermediate petals is near between 65B and 65C.

The under and upper surface color of the inner petals is near between 65B and 65C. The upper surface color of the inner petals is near between 65B and 65C.

The general tonality of the newly opened flower is between 65B and 62C.

MALE REPRODUCTIVE ORGANS

Stamens are many in number (average about 100) and are arranged irregularly about the pistils. The filaments are medium to length (about 1.25 to about 1.50 cm.) most with anthers. Filaments are near between 17B and 17C in color. The anthers are somewhat medium to for the class and all open approximately at the same time. Anther color is near between 17C fading to 18a. Pollen is moderate to abundant and between 12a and 11a in color.

FEMALE REPRODUCTIVE ORGANS

Pistils vary in number (average about 150). The styles are uneven, in length (about 1.25 to about 1.50 cm.), average in caliper, and somewhat loosely separated. Stigma color is near between 6c and 6d. Style color is near between 6b and 6c. Ovaries are enclosed in the calyx, although few may protrude from the calyx.

Hips have not been observed on this variety when grown in La Verne, Calif.

FOLIAGE

The compound leaves are usually comprised of three to five leaflets and are borne abundantly in normal quantities. The five-leaflet leaves are about 2.5 to about 3 cm. in length and about to about 1.5 cm. in width at the widest point, moderately crisp in texture, and matte in finish. Their margins are usually somewhat serrate and irregular.

The upper and under surface color of the mature leaf is near 139a. The under surface color of the mature leaf is near 137b. The upper and under surface color of the young leaf is near between 137c and 137d. The under surface color of the young leaf is near between 137b and 137c, sometimes lightly heavily suffused with near 137d.

The rachis is somewhat heavy in caliper and somewhat smooth. The upper side is moderately grooved with few hairs and stipitate glands and prickles on the edges of the grooves. The under side of the rachis is moderately smooth rough with some hairs and stipitate glands and moderately small prickles. The rachis color is near 147c.

The petiole is average to in caliper and somewhat smooth. The upper side shallowly grooved with few some many hairs and stipitate glands and prickles on the edges of the grooves. The under side of the rachis is somewhat smooth with some many hairs and stipitate glands and moderately medium prickles. The petiole is about 1.5 to about 2.5 cm. in length and about 1 mm in diameter. The petiole color is near between 137b and 137c.

The plant displays an average degree of resistance to powdery mildew and rust as compared to other commercial varieties grown under comparable conditions in La Verne, Calif. The plant's winter hardiness and drought/heat tolerance are yet to be determined.

GROWTH

The plant has a upright height to tall growth habit (about 150 to about 180 cm. in height and about 100 to about 120 cm. spread at the widest point), with full branching. It displays vigorous growth and the canes are of heavy caliper for the class.

The color of the major stems is near between 138b and 138c. They bear several large prickles that are about 1.75 to about 2 cm. in length. The large prickles are almost straight and hooked slightly downward with a somewhat medium length to rounded base; prickle color is near between 11b. The major stem bears several small prickles of similar shape and coloration and which are near 11b in color.

I claim:

1. A new and distinct Hybrid Tea rose plant of the variety substantially as described and illustrated herein.

* * * * *